United States Patent [19]

Rammler

[11] Patent Number: 5,078,697
[45] Date of Patent: Jan. 7, 1992

[54] SYRINGE NEEDLE GUARD

[76] Inventor: David H. Rammler, 30 Oak Hill Dr., Woodside, Calif. 94062

[21] Appl. No.: 619,201

[22] Filed: Nov. 28, 1990

[51] Int. Cl.⁵ .............................................. A61M 5/32
[52] U.S. Cl. ..................................... 604/198; 604/263
[58] Field of Search ................ 604/198, 263, 192, 187

[56] References Cited

U.S. PATENT DOCUMENTS 4,139,009 2/1979 Alvarez ................................ 604/198
4,735,618 4/1988 Hagen ................................... 604/198

Primary Examiner—John D. Yasko
Attorney, Agent, or Firm—Bertram I. Rowland

[57] ABSTRACT

Syringe needle protective devices are provided, comprising a mounting, a protective collar, and flexible ribs joining the collar to the mounting. When the needle is injected, the collar retracts, with the flexible ribs extending outwardly. An outer collar may be provided to restore and lock the collar to its original position, when the needle is withdrawn from an injection.

6 Claims, 1 Drawing Sheet

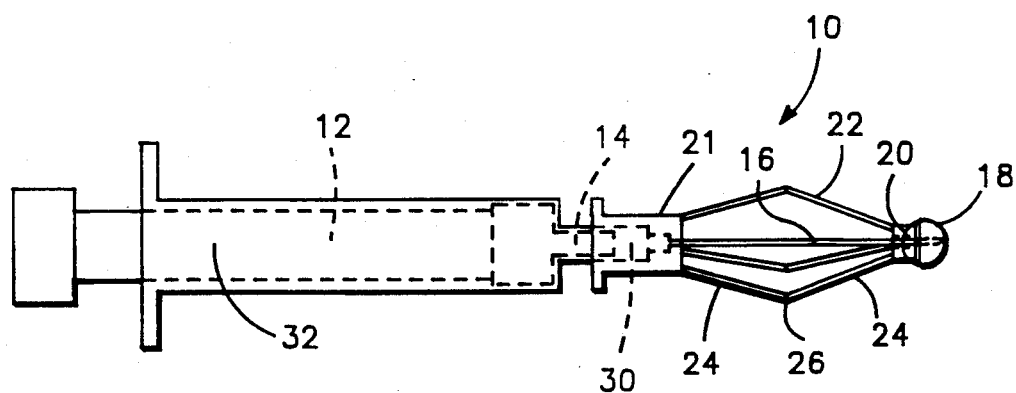
FIG.—1
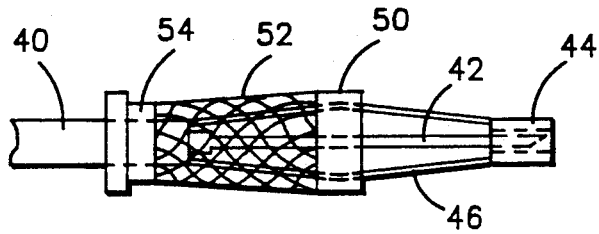
FIG.—2
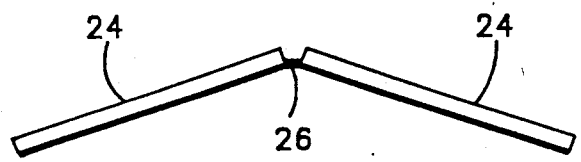
FIG.—3
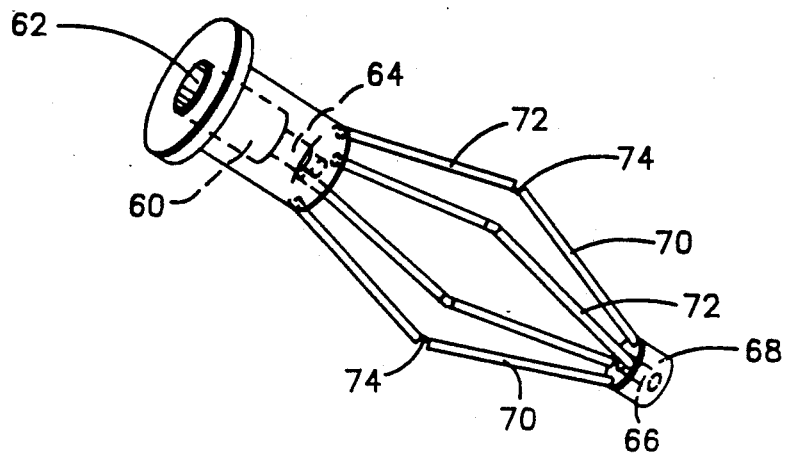
FIG.—4

SYRINGE NEEDLE GUARD

TECHNICAL FIELD

The field of this invention is protective devices for sharps.

BACKGROUND

There is increasing concern about the use of sharps by medical personnel, as the medical personnel work with a wide variety of people who may be infected with highly contagious organisms. By sharps is intended syringe needles, scalpels, or other instrumentality which may readily pierce the skin and result in bleeding. Concerns with infection of viruses, such as HIV, HTLV-1 and hepatitis has caused increasing concern in the medical environment. Nevertheless, despite the increasing degree of care, there is always a possibility of a cut or a stab.

There is, therefore, substantial interest in being able to provide mechanisms whereby the technician using a sharp may be substantially protected from scratches, cuts or stabs.

SUMMARY OF THE INVENTION

A syringe needle and guard is provided comprising a syringe mounting, a needle extending from the mounting, a collar, and flexible ribs connecting the collar to the mounting. An outer gauze cover extending from the mounting to a second collar may be used to partially cover the flexible ribs.

BRIEF DESCRIPTION OF THE DRAWINGS

FIG. 1 is a side view of the subject invention, partially in cross section;

FIG. 2 is a side view of another embodiment of the subject invention;

FIG. 3 is a perspective view of a flexible rib; and

FIG. 4 is a perspective view of the subject invention with the flexible ribs extended.

DESCRIPTION OF THE SPECIFIC EMBODIMENTS

A syringe needle guard is provided to prevent accidental scratching or stabbing of a person using the syringe and needle. The guard and needle may be a single unit or the guard may be separate from the needle, being removably mounted on the needle. The guard provides for a protective collar which surrounds the needle point and prevents any contact with the needle point, except when the needle is injected into a soft resistant substance, such as skin, tissue, elastomeric materials, such as stoppers, septums, or the like. By injecting the needle into a resistant material, as the needle moves through the resistant material, the collar moves up the needle, allowing the needle to extend as far as desired.

The needle guard may provide for a mounting onto the syringe outlet, such as a LeurLok mounting or other convenient mounting. The particular mounting which is employed may be conventional, where the mounting may be of any convenient material, such as metal, plastic, particularly plastic capable of molding, and the like.

Alternatively, the guard may fit on the syringe mounting portion of the needle, so as to provide a housing in which the mounting portion of the needle fits. Thus, a channel would be provided which fits over the needle and is held in place by friction or may provide for adhesive interaction between the guard and the syringe mounting.

The mounting is connected to the protective collar by a plurality of strips or flexible ribs, which bend and extend outwardly as the collar is moved up the needle. The appearance of the guard is much like a Molly screw, where the flexible ribs may be respectively, retractable and extendable, so as to ensure that the protective collar surrounds the needle point, at any time the needle is removed from the substrate into which it is extended. The flexible ribs will usually include a centrally located flexible bridge.

The ribs may be of any convenient material, most conveniently plastic, which may allow for the guard, either by itself or in conjunction with the needle, to be molded as a unit. Thus, the syringe mounting, flexible ribs and collar may be made of the same plastic. A variety of plastics may be used, such as polyethylene, polypropylene, Delrin, polycarbonate, or the like.

Optionally, further protection may be achieved by having an outer collar which surrounds the ribs below the point where the ribs bend outwardly and is connected by a convenient means to the syringe mounting. This second collar or outer collar may be used to ensure that the ribs are in their extended position and the collar surrounds the needle point to prevent any scratches or punctures.

For further understanding of the invention, the drawings will now be considered. In FIG. 1, the guard device 10 is mounted on syringe 12 at tubular outlet 14. The guard is shown in partially retracted position with needle 16 extending through septum 18. The collar 20 is retracted moving up the needle with ribs 22 having two spines 24 joined by flexible bridge 26 which allows for the bending of the ribs 22 at the site of the bridge 26.

The syringe mounting comprises housing 28 with channel 30 which allows for the flow of fluid from the tubular outlet 14 into needle 16. The mounting 28 is molded to include needle 16 as part of the housing.

The syringe comprises plunger 32 which can be used to withdraw and transfer a measured amount of fluid through needle 16.

In FIG. 2 is an alternative embodiment of the subject invention, comprising mounting 40, needle 42, collar 44 and ribs 46. In addition, a further protective device is provided with a protective collar 50 joined to gauze 52, which connects the collar to ring 54 which sits on mounting 40. The ring 54 is conveniently irreversibly fastened to mounting 40 by any convenient means. When the collar 44 rises upwards on needle 42 and the ribs 46 extend, the outer protective collar 50 will move up and allow the ribs to bend. However, when the ribs 46 are in their extended position, the collar moves downwardly and prevents the ribs from moving as a result of a sidewise force.

In FIG. 4 is shown a guard without the needle, where the mounting 60, can be mounted on the syringe needle sleeve. In this manner, the needle will extend through the mounting 60 which has channel 62 to fit over the sleeve of the needle, where the needle will extend through upper channel 64 and lower channel 66 of collar 68. Ribs 70 have individual spines 72 joined by bridging links 74 for retraction. When the protective device is required, it is mounted on the needle sleeve with the needle extending through the collar 68 and is ready for use.

The subject device provides for a simple, easily fabricated device to provide protection against adventitious scratches or punctures resulting from syringe needles. In this way, the user may be secure in the knowledge that blood or other infectious physiological fluid which may be withdrawn will not be able to be introduced into the user through the skin. The subject device may find wide use in hospitals, blood banks, doctors offices, and the like.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A syringe needle guard comprising:
   means for affixing to a syringe;
   a first collar;
   a plurality of flexible ribs connecting said affixing means and said collar, whereby when said needle guard is mounted on a syringe and a needle extends from said syringe to said first collar, injecting said needle into a resistant substrate results in retraction of said collar and outward expansion of said ribs and removal of said needle from said resistant substrate results in restoration of said first collar to substantially its original position; and
   an outer collar positioned adjacent said first collar and fastened to said affixing means by flexible material, so as to be able to retract with said first collar.

2. A guard according to claim 1, wherein said flexible material is gauze.

3. A syringe needle guard and needle comprising:
   housing means for affixing to a syringe comprising a central channel;
   a needle attached to said housing means in fluid receiving relationship with said channel;
   a first collar surrounding the end of said needle;
   a plurality of flexible ribs connecting said affixing means and said collar, whereby when said needle guard is mounted on a syringe and a needle extends from said syringe to said first collar, injecting said needle into a resistant substrate results in retraction of said collar and outward expansion of said ribs and removal of said needle from said resistant substrate results in restoration of said first collar to substantially its original position; and
   an outer collar positioned adjacent said first collar and fastened to said affixing means by flexible material, so as to be able to retract with said first collar.

4. A guard according to claim 3, comprising three ribs, and said ribs comprise a flexible bridge substantially centrally located.

5. A guard according to claim 3, wherein said affixing means, first collar and ribs are comprised of plastic.

6. A guard according to claim 3, wherein said flexible material is gauze.

* * * * *